(12) United States Patent
Giuliani et al.

(10) Patent No.: US 8,877,738 B2
(45) Date of Patent: Nov. 4, 2014

(54) ANTIPATHOGENIC PEPTIDES

(75) Inventors: Andrea Giuliani, Colleretto Giacosa (IT); Giovanna Pirri, Colleretto Giacosa (IT); Lorena Pizzuto, Colleretto Giacosa (IT); Santo Landolfo, Turin (IT); Giorgio Gribaudo, Turin (IT); David Lembo, Orbassano (IT); Davide Gibellini, Bologna (IT)

(73) Assignee: Spiderbiotech S.r.L., Colleretto Giacoase (IT)

( * ) Notice: Subject to any disclaimer, the term of this patent is extended or adjusted under 35 U.S.C. 154(b) by 84 days.

(21) Appl. No.: 13/387,154

(22) PCT Filed: Aug. 5, 2010

(86) PCT No.: PCT/EP2010/061424
§ 371 (c)(1),
(2), (4) Date: Jan. 26, 2012

(87) PCT Pub. No.: WO2011/015628
PCT Pub. Date: Feb. 10, 2011

(65) Prior Publication Data
US 2012/0121623 A1    May 17, 2012

(30) Foreign Application Priority Data
Aug. 5, 2009   (IT) .............. MI2009A1425

(51) Int. Cl.
| A61K 38/00 | (2006.01) |
| A61P 31/04 | (2006.01) |
| A61P 31/12 | (2006.01) |
| A61P 31/22 | (2006.01) |
| A61P 31/18 | (2006.01) |
| C07K 7/08 | (2006.01) |
| C07K 14/00 | (2006.01) |
| C07K 7/06 | (2006.01) |

(52) U.S. Cl.
CPC ............... *C07K 7/08* (2013.01); *C07K 14/001* (2013.01); *C07K 7/06* (2013.01); *A61K 38/00* (2013.01)
USPC .............. 514/110; 514/3.8; 514/3.7; 514/2.9; 514/2.4; 514/2.3; 424/185.1; 424/280.1; 530/324; 530/325; 530/326; 530/327

(58) Field of Classification Search
CPC ....... A61K 38/16; A61K 38/03; A61K 38/04; A61K 31/18; A61K 31/74; C08L 23/00; C07K 1/006; C07K 14/00; C07K 14/001; C07K 7/04; C07K 7/08; C07K 4/00
USPC .......................................... 514/110
See application file for complete search history.

(56) References Cited

U.S. PATENT DOCUMENTS

2004/0214272 A1   10/2004   La Rosa et al.

FOREIGN PATENT DOCUMENTS

| CA | WO 2008/022444 | * | 2/2008 | ............. C12N 15/12 |
| WO | 0024782 A2 | | 5/2000 | |
| WO | WO/03/084477 | * | 10/2003 | |
| WO | 2005081687 A2 | | 9/2005 | |
| WO | 2006010057 A2 | | 1/2006 | |
| WO | 2009024445 A1 | | 2/2009 | |

OTHER PUBLICATIONS

Sadler et al., Reviews in Molecular Biotechnology (2002) 90, 195-229.*
Bartlett, A Guide to Primary Care of People with HIV/AIDS, Chapter 5 (2005) Aids Education Online. Retrieved from ftp://ftp.hrsa.gov/hab/PCGchap5.pdf on Dec. 21, 2012).*
Frecer, "QSAR analysis of antimicrobial and haemolytic effects of cyclic cationic antimicrobial peptides derived from protegrin-1", Bioorganic & Medicinal Chemistry,14 (2006), pp. 6065-6074.

* cited by examiner

*Primary Examiner* — Karlheinz R Skowronek
*Assistant Examiner* — Catherine Mader
(74) *Attorney, Agent, or Firm* — Rothwell, Figg, Ernst & Manbeck, P.C.

(57) ABSTRACT

The present invention relates to monomeric and multimeric peptidic compounds which have antipathogenic, in particular antiviral or/and antibacterial activity. In a preferred aspect, the peptide compounds of the invention have an activity in respect of a broad spectrum of viruses, both DNA and RNA viruses, irrespective of whether they possess virus envelope or not. Further, the present invention refers to compositions comprising said peptidic compounds for medical use, i.e. for the treatment or prevention of pathogenic, in particular viral or/and bacterial infections.

29 Claims, 6 Drawing Sheets

SEQUENCE LISTING

<160> NUMBER OF SEQ ID NOS: 2

<210> SEQ ID NO 1
<211> LENGTH: 9
<212> TYPE: PRT
<213> ORGANISM: Artificial
<220> FEATURE:
<223> OTHER INFORMATION: peptidic compound

<400> SEQUENCE: 1

Ala Ser Leu Arg Val Arg Ile Lys Lys
1               5

<210> SEQ ID NO 2
<211> LENGTH: 10
<212> TYPE: PRT
<213> ORGANISM: Artificial
<220> FEATURE:
<223> OTHER INFORMATION: peptidic compound

<400> SEQUENCE: 2

Ala Ser Leu Arg Val Arg Ile Lys Lys Gln
1               5                   10

ANTIPATHOGENIC PEPTIDES

CROSS REFERENCE TO RELATED APPLICATION

This application is a 35 U.S.C. 371 National Phase Entry Application from PCT/EP2010/061424, filed Aug. 5, 2010, which claims the benefit of Italian Patent Application No. MI2009A001425 filed on Aug. 5, 2009, the disclosure of which is incorporated herein in its entirety by reference.

The present invention relates to monomeric and multimeric peptidic compounds which have antipathogenic, in particular antiviral or/and antibacterial activity. In a preferred aspect, the peptide compounds of the invention have an activity in respect of a broad spectrum of viruses, both DNA and RNA viruses, irrespective of whether they possess virus envelope or not. Further, the present invention refers to compositions comprising said peptidic compounds for medical use, i.e. for the treatment or prevention of pathogenic, in particular viral or/and bacterial infections.

Bacterial and viral infections of humans and domestic animals cost billions of dollars every year. Medical science is constantly searching for new and more powerful agents to prevent and treat bacterial and viral infections. Despite a wide range of drugs against bacterial infections is available for the treatment of diseases caused by bacteria, the treatment of viral diseases is often difficult and few of them are really effective. Indeed, viruses enter mammalian cells, where they perform many of their functions such as transcription and translation of viral proteins and replication of the viral genome. Thus, viruses are able to evade both the host's immune system and the direct action of medicines administered to the host. Therefore, there is a serious need for developing new and effective antiviral agents.

TABLE 1

| Virus | Host | Diseases |
|---|---|---|
| HSV 1 | Humans | gingivostomatitis, herpes labialis, herpes genitalis, and herpes keratitis |
| HSV2 | Humans | herpes labialis, herpes genitalis, genital lesions, encephalitis |
| HCMV | Humans | retinitis, mononucleosis, hepatitis, pneumonitis, colitis, brain damage and hearing loss in congenital infection |
| HIV | Humans | Acquired immunodeficiency syndrome (AIDS), opportunistic infection-related diseases, tumors, immunodeficiency, anemia, thrombocytopenia, pneumonitis, encephalopathy, gastroenteropathy, nephropathy, wasting, rheumatologic syndromes |
| HPV | Humans | cervical dysplasia, ano-genital warts |

Herpes simplex virus type 1 (HSV-1) is a prevalent human pathogen causing painful recurrent blisters around the mouth (herpes labialis) and an increasing proportion of recurrent genital infections (herpes genitalis). Herpes simplex virus type 2 (HSV-2) is commonly associated with herpes genitalis. Genital herpes infection is one of the world's most prevalent sexually transmitted diseases (STDs) and a major public health problem among young adults. HSV interacts with epithelial cells and productively replicates in this cell type. Then HSV is transported within the axons of sensory nerve endings at the infection site to the peripheral ganglion, where the virus establishes latent infection (Garner, 2003). The currently available topical treatments for herpes are largely ineffective and oral (systemic) therapies pose concerns in the development of drug-resistant organisms, particularly in immunocompromised patients where recurrences of genital herpes are common.

Human cytomegalovirus (HCMV) is a member of the beta subfamily of herpesviruses; HCMV has also been designated as human herpesvirus 5 (HHV5). HCMV is a ubiquitous virus infection with a worldwide distribution with a seroprevalence between 30% in some areas of North America and North Europe to nearly 100% in children and adults from undeveloped countries in Africa, Asia and South America. HCMV infection in normal immunocompetent hosts is generally subclinical, however, it may cause severe diseases in the absence of an effective immune response, as in immunologically immature and immunocompromised patients. HCMV has been associated with disease in three groups of immunocompromised hosts: 1) fetuses secondary to immunological immaturity; 2) allograft recipients secondary to cytotoxic antirejection agents; 3) HIV infected patients with loss of CD4+ and adaptive immune responses. The major organ systems generally clinically affected are: the central nervous system (CNS), the lungs, and the gastrointestinal tract. Retinitis is the most frequent CNS infection directly attributable to HCMV replication, and the most sight-threatening. Current therapy which includes Ganciclovir (Cytovene), Foscarnet (Foscavir) and HPMPC (Cidofovir), all suffer from dose-related toxicities and the development of drug resistant mutants (Landolfo et al., 2003).

Human papillomaviruses (HPV) are members of the Papillomaviridae family of DNA viruses. More than 100 HPV types have been identified so far, over 30 of which infect the genital area (Lowy and Howley, 2001). Genital HPV infections are estimated to be the most common sexually transmitted infection. Although the majority of infections cause no symptoms and are self-limiting, genital HPV have become a major public health concern because persistent infection with certain types can cause cervical cancer which kills about 250,000 women worldwide each year (Bosch and de Sanjose, 2003). Current treatments are ablative and directed to abnormal cells associated with HPV rather than the virus itself; no direct antiviral treatment is available. The prevention of genital HPV infection is essential for reducing the prevalence of genital warts and abnormal Pap tests, as well as cervical cancer. Since male condoms have been reported to provide only partial protection against HPV transmission they cannot be recommended as a primary prevention strategy (Manhart and Koutsky, 2002).

Recently, a highly effective vaccine was approved to prevent infections by four HPV types that together cause about 70% of cervical cancers (HPV-16 and HPV-18) and 90% of genital warts (HPV-6 and HPV-11) worldwide (Garland et al., 2007). However, women may remain exposed to the risk of becoming infected with genotypes of high-risk HPV (HPV-31, HPV-33, HPV-45 etc) that can cause cervical cancer but are not targeted by the current vaccine. Moreover, the vaccine is relatively expensive and it may not be initially available to all women, especially those in the developing countries. In this scenario, a topical microbicide, a compound that could block the full spectrum of genital HPV infections at the portal of entry, would be a useful complement to vaccination programmes.

Human immunodeficiency virus (HIV) is a member of Retroviridae family and mainly infects CD4+ T lymphocytes and macrophages. HIV induces a persistent, lifelong infection, which, if untreated, evolves to acquired immunodeficiency syndrome (AIDS) and death of the infected individual (Quinn, 2008). Over the past 25 years, significant advances have been achieved in the development of antiretroviral agents. In particular, the advent of highly active antiretroviral therapy (HAART), based on treatment of HIV patients by antiretroviral drugs used in combination, can strongly suppress viral replication and prevent progression to AIDS even though is not fully able to eradicate the infection (Marsden and Zack, 2009). The major drawback of antiretroviral therapy is the appearance of specific antiretroviral resistance that may arise during long lasting treatment of HIV individuals eliciting a progressive failure of therapy effectiveness (Wilson and Gallant 2009). Hence it is pivotal to find new antiretroviral compounds to increase the arsenal of "magic bullets" directed towards the different phases of viral replication cycle in order to augment the complexity and flexibility of antiretroviral therapy.

Natural antimicrobial peptides (AMPs) have a variety of interesting biological activities including antibacterial, antifungal, antiparasitic, antitumoral, and antiviral activities (Giuliani et al., 2007). It is believed that they have multiple targets, including the cytoplasmic membrane and the processes of cell division and macromolecule synthesis (Buck et al., 2005). The importance of AMPs extends beyond their direct antimicrobial activity, as their broad biological activities indicate they are effector molecules providing communication between innate and adaptive immune systems (Yang et al., 2002).

The antiviral effects of cationic polypeptides on herpes simplex virus type 1 (HSV) as well as on a variety of other viruses, including tobacco mosaic, mumps, Newcastle disease, and influenza, have been well documented (Langeland et al., 1988). In another study, magainin class of peptides, potent antimicrobial cationic peptides originally isolated from the skin and granular secretions of the African clawed frog *Xenopus laevis*, and particularly derivatives that are lysine-rich and possess octanoyl groups, are capable of exerting a direct antiviral effect on HSV.

WO 2006/018431 discloses a peptide sequence from the β-chain of human haemoglobin corresponding to the sequence region 112-147 of human β-haemoglobin, effective against HSV-2 in vivo.

In recent years, dendritic molecules, or dendrimers, have been found to have increasing biotechnology or pharmaceutical applications. A dendrimer is a large highly branched macromolecule that is synthesized from a polyfunctional core. Dendrimer molecules have been synthesized that contain functional groups in the surface layer that can form complexes with cell or viral receptors, disrupting normal virus-cell interactions, including the initial binding of virus to the cell (Bourne et al., 2000).

A particular subclass of dendrimers is represented by peptide dendrimers or wedge-like branched macromolecules consisting of a peptidyl branching core and/or covalently attached surface functional units (Niederhafner et al., 2005).

WO 02/079299 describes a new class of polyvalent, highly branched molecules with a definite envelope of polyanionic groups which have been found to exhibit significant antiviral activity, particularly against a broad spectrum of viral and microbial pathogens involved in sexually transmitted disease. These compounds are synthesized from monomeric building blocks with multiple branches or tree-like structures. The outside surface is endowed with a number of functional groups that lead to recognition by a biological receptor.

Dendrimers are attractive as potential new therapeutics because of their size (nanomolar), their ease of preparation and functionalization, and their ability to display multiple copies of surface groups (multivalency) for biological recognition processes, in particular in anti-viral applications.

The present invention provides methods for using and making novel antipathogenic peptidic compounds to treat and/or prevent viral or/and bacterial infections.

A subject-matter of the present invention is a peptidic compound having a length of up to 35 amino acid residues comprising an amino acid sequence represented by the general formula (I):

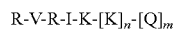

wherein

R is an amino acid residue with an arginine side chain or an N-alkyl substituted guanidine side chain, particularly L-arginine, V and I are amino acid residues independently selected from:
(i) an amino acid residue with a valine side chain, particularly L-valine,
(ii) an amino acid residue with an isoleucine side chain, particularly L-isoleucine,
(iii) an amino acid residue, which has a linear straight-chain saturated or unsaturated side chain with at least three C-atoms, preferably with 3-10 C-atoms, particularly norleucine, 2-aminopentanoic acid, 2-aminooctanoic, 2-aminodecanoic acid or 2-aminododecanoic acid,
(iv) an amino acid residue, which has a branched saturated or unsaturated side chain with at least three C-atoms, preferably with 3-10 C-atoms, particularly tert-leucine, 5-methyl norleucine or homoisoleucine (4-methyl norleucine);
(v) an amino acid residue, which has a cyclic saturated or unsaturated side-chain with at least 3 C-atoms, preferably with 3-10 C-atoms, which is particularly selected from cyclic residues with 3-6 ring atoms, optionally comprising a C=C double bond such as cyclopropyl, cyclobutyl, cyclobutenyl, cyclopentyl, cyclopentenyl, cyclohexyl, cyclohexenyl, optionally substituted in any ring positions with aliphatic groups, preferably aliphatic groups having 1-10 C-atoms, more preferably 1-8 C-atoms, even more preferably 1-6 C-atoms and particularly preferably methyl, ethyl, isopropyl, n-propyl, n-butyl, isobutyl, such as norfuranomycin, carbafuranomycin, cyclopentylglycine, cyclopentenyl-glycine or cyclohexenylglycine.

K is an amino acid residue with a lysine side chain, particularly L-lysine, or another amino acid residue with a positively charged side chain, particularly ornithine or 2,4-diaminobutyric acid;

Q is an amino acid residue with a glutamine side chain, particularly, L-glutamine, and m and n are independently 0 or 1.

Preferably, the amino acid residue V of formula (I) is an amino acid residue with a valine side chain, particularly L-valine, and the amino acid residue I of formula (I) is an amino acid residue with an isoleucine side chain, particularly L-isoleucine.

The peptidic compound may comprise L- and/or D-amino acid residue building blocks.

The sequences of the peptidic compounds of the invention are written from the N-terminus on the left to the C-terminus on the right.

In a preferred embodiment, the present invention relates to a peptidic compound having a length of up to 35 amino acid residues comprising an amino acid sequence represented by the general formula (II):

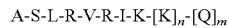

wherein R, K, Q, V, I, n and m are as defined above, and
wherein A is an amino acid residue with an alanine side
  chain, particularly L-alanine,
S is an amino acid residue with a hydroxyl-substituted
  aliphatic or aromatic side chain, particularly an amino
  acid residue with a serine side chain, more particularly
  L-serine,
L is an amino acid residue selected from
  (i) an amino acid residue with a leucine side chain, particularly L-leucine,
  (ii) an amino acid residue with an isoleucine side chain, particularly L-isoleucine,
  (iii) an amino acid residue, which has a linear straight-chain saturated or unsaturated side chain with at least three C-atoms, preferably with 3-10 C-atoms, particularly norleucine, 2-aminopentanoic acid, 2-aminooctanoic, 2-aminodecanoic acid or 2-aminododecanoic acid,
  (iv) an amino acid residue, which has a branched saturated or unsaturated side chain with at least three C-atoms, preferably with 3-10 C-atoms, particularly tert-leucine, 5-methyl norleucine or homoisoleucine (4-methyl norleucine),
  (v) an amino acid residue, which has a cyclic saturated or unsaturated side-chain with at least 3 C-atoms, preferably with 3-10 C-atoms, which is particularly selected from cyclic residues with 3-6 ring atoms, optionally comprising a C=C double bond such as cyclopropyl, cyclobutyl, cyclobutenyl, cyclopentyl, cyclopentenyl, cyclohexyl, cyclohexenyl, optionally substituted in any ring positions with aliphatic groups, preferably aliphatic groups having 1-10 C-atoms, more preferably 1-8 C-atoms, even more preferably 1-6 C-atoms and particularly preferably methyl, ethyl, isopropyl, n-propyl, n-butyl, isobutyl, such as norfuranomycin, carbafuranomycin, cyclopentylglycine, cyclopentenyl-glycine or cyclohexenylglycine.

In a very preferred embodiment, the peptidic compounds of the present invention comprise an amino acid sequence selected from A-S-L-R-V-R-I-K-K (IIa) and A-S-L-R-V-R-I-K-K-Q (IIb), wherein R, K, Q, V, I, A, L and S are as defined above, in particular wherein
R is an amino acid residue with an arginine side chain or an N-alkyl substituted guanidine side chain, particularly L-arginine,
V is an amino acid residue with a valine side chain, particularly L-valine,
I is an amino acid residue with an isoleucine side chain, particularly L-isoleucine, and
L is an amino acid residue with a leucine side chain, particularly L-leucine.

In a very preferred embodiment of formulae IIa and IIb, A is alanine, S is serine, L is leucine, R is arginine, V is valine, I is isoleucine, K is lysine, and Q is glutamine (SEQ ID NO:1 and SEQ ID NO:2).

In a preferred embodiment of the invention, the antipathogenic, in particular antiviral or/and antibacterial peptide compounds may have an amphipathic structure.

In a further preferred embodiment, the present invention refers to a multimeric compound comprising a plurality of peptidic compounds as defined above, wherein the individual peptidic compounds are covalently linked, e.g. by multifunctional, e.g. di- or trifunctional moieties, such as di- or trifunctional amino acids.

The present invention refers to peptidic compounds. The term "peptidic compounds" encompasses compounds, which at least partially comprise amino acid building blocks or analogues thereof, which are linked by covalent bonds, preferably carboxamide bonds. The building blocks are preferably selected from amino-carboxylic acids, e.g. α-amino carboxylic acids or other types of carboxylic acids, e.g. β- or even ω-amino carboxylic acids. The amino acid building blocks may be selected from genetically encoded L-α-amino carboxylic acids and/or their D-enantiomers and/or from non-naturally occurring amino acid building blocks.

Subject-matter of the invention are also peptidic compound variants, wherein single amino acid building blocks are modified. In particular said building block modification comprises the substitution of single amino acids, in particular by conservative substitution, wherein an amino acid is replaced with another amino acid of similar chemical structure without altering the functionality of the peptides. Furthermore, according to the invention, also single amino acid modification may comprise the substitution of single amino acids with amino acid mimetics.

The amino acid building blocks may also be selected from amino acid mimetics. Amino acid mimetics refer to chemical compounds that have a structure that is different from the general chemical structure of an amino acid, but which functions in a manner similar to a naturally occurring amino acid. These non-natural residues are well described in the scientific and patent literature; a few exemplary non-natural residues useful as mimetics of natural amino acid residues and guidelines are described below. Mimetics of aromatic amino acids are, e.g., D- or L-naphtylalanine; D- or L-phenylglycine; D- or L-2 thieneylalanine; D- or L-, 2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluorophenylalanine; D- or L-p-biphenylphenylalanine; D- or L-p-methoxy-biphenylphenylalanine; D- or L-2-indole(alkyl) alanines; and, D- or L-alkylalanines. In this context, the term "alkyl" means a substituted or unsubstituted methyl, ethyl, propyl, hexyl, butyl, pentyl, isopropyl, iso-butyl, sec-isobutyl or iso-pentyl. Aromatic rings of a non-natural amino acid include, e.g., thiazolyl, thiophenyl, pyrazolyl, benzimidazolyl, naphthyl, furanyl, pyrrolyl, and pyridyl aromatic rings.

The peptidic compounds of the invention, as defined above, may include all "mimetic" and "peptidomimetic" forms. The terms "mimetic" and "peptidomimetic" refer to a synthetic chemical compound that has substantially the same structural and/or functional characteristics of the peptidic compound of the invention. The mimetic can be either entirely composed of synthetic, non-natural analogues of amino acids, or, is a chimeric molecule of partly natural peptide amino acids and partly non-natural analogous of amino acids. The mimetic can also incorporate any amount of natural amino acid conservative substitutions so long as such substitutions do not also substantially alter the mimetic's structure and/or activity.

The individual building blocks of the peptidic compounds are linked by natural amide bond ("peptide bond") linkages or other covalent bonds, e.g. carboxamide, carbamate, ester, thioester, ether, thioether, tetrazole, thiazole, retroamide and thioamide bonds. The peptidic compounds of the present invention may be linear or cyclic. Monomeric peptidic compounds have a length up to 35 amino acid residues, and preferably a length of at least 8, more preferably at least 9 or 10, and up to 15 amino acid building blocks.

In a preferred embodiment, the invention refers to a multimeric compound comprising a plurality of peptidic compounds as described above. For example, a multimeric compound of the present invention may comprise 2, 3, 4, 5, 6, 7, 8 copies or more of the peptidic compounds. The multimeric compound may comprise the peptidic compounds multimerized on a matrix, e.g. a matrix based on a polypeptide, a mono-, oligo- or polysaccharide or an organic polymer, preferably a linear organic polymer. For example, the matrix may be selected from poly(N-alkyl(meth)acrylamide), poly(N,N-dialkyl(meth)acrylamide), polymelamine, dextrane, cyclodextrine, polyethyleneglycol and/or polyvinylpyrrolidone. The coupling of the peptidic compounds to the matrix preferably occurs via the N- and/or C-termini of the peptidic compound, e.g. using homo- and/or hetero-bifunctional linkers which allow coupling to reactive groups, e.g. hydroxy-, amino-, thiol- or carboxyl groups on the matrix.

In a further preferred embodiment, the multimeric compound has a branched, particularly a dendritic structure.

In a still further embodiment, the multimeric compound is selected from:

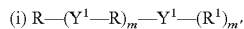  (IIIa)

wherein $R^1$ is a peptidic compound as defined above or in any one of claims 1-5, Y.sup.1 is a covalent bond or a bifunctional linker, e.g. a dialcohol such as propylene glycol, a dicarboxylic acid such as succinic acid, a diamine such as ethylene diamine, an amino acid, a hydroxy carboxylic acid, e.g. a hydroxy alcanoic acid, or a diisocyanate, and m is 0, or a positive whole number, in particular 1, 2, 3, 4, 5 or 6, and m' is 0 or 1,

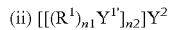  (IIIb)

wherein $R^1$ is a peptidic compound as defined above or in any one of claims 1-5,
$Y^{1'}$ is in each case independently a linker having a functionality of at least 3, e.g. a trifunctional amino acid such as lysine, ornithine, 2,4-diaminobutyric acid, nor-lysine, aminoalanine, aspartic acid or glutamic acid, and
$Y^2$ is a linker having a functionality of at least 2, and
$n_1$ and $n_2$ in each case independently are a whole number of at least 2, preferably 2, 3 or 4, more preferably 2,

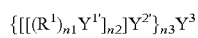  (IIIc)

wherein $R^1$ is a peptidic compound as defined above or in any one of claims 1-5,
$Y^{1'}$ and $Y^{2'}$ are in each case independent linkers having a functionality of at least 3, e.g. a trifunctional amino acid such as lysine, ornithine, 2,4-diaminobutyric acid, nor-lysine, aminoalanine, aspartic acid or glutamic acid,
$Y^3$ is a linker having a functionality of at least 2 and
$n_1$, $n_2$ and $n_3$ are in each case independently whole numbers of at least 2, preferably 2, 3 or 4, more preferably 2.

The multimeric compound (IIIa) is a multimeric linear compound, wherein a plurality of peptidic compounds are connected via covalent bonds and/or homo- or hetero-bifunctional linkers $Y^1$. Preferably, the multimeric compound comprises up to 8, more preferably up to 4 units of peptidic compounds (I) or (II).

The multimeric compounds (IIIb) and (IIIc) are branched compounds, wherein individual peptidic units $R^1$ are connected via linkers having a functionality of at least 3. In a preferred embodiment, the multimeric compound (IIIb) comprises 4 peptidic units and has the structure:

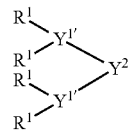

In a further preferred embodiment, the multimeric compound (IIIc) comprises 8 peptidic units and has the structure:

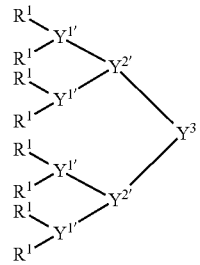

The linker $Y^2$ of the multimer compound (IIIb) and the linker $Y^3$ of the multimeric compound (IIIc) may be preferably a linker having a functionality of 3, preferably a trifunctional amino acid linker, most preferably a lysine. In a still preferred embodiment, the linkers $Y^2$ and $Y^3$ are bond to further amino acid residues, preferably to 1, 2, 3 or 4 amino acid residues, which may be selected from α-, β- or even ω-amino acid residues. In a very preferred embodiment, the further amino acid residue bond to the $Y^2$ and/or $Y^3$ linker is a β-amino acid residue, most preferably a β-alanine residue.

In a preferred embodiment of the invention, the multimeric compound (IIIb) has the structure:

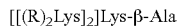

Specific examples of multimeric peptidic compounds according to the present invention comprise a monomeric peptidic compound unit as described above, preferably an amino acid sequence as defined in SEQ ID NO: 1 or 2 and are represented by the structures:

  (IV)

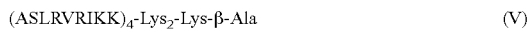  (V)

Wherein β-Ala is a naturally occurring β-alanine amino acid, in which the amino group is at the β-position from the carboxylate group residue and wherein the above peptides are optionally amidated at their C-termini.

In a still further embodiment of the present invention, the peptidic and multimeric compounds comprise at least one modification, particularly selected from a lipid, amide, ester, acyl and/or alkyl moiety attached thereto, e.g. attached to an N-terminal group, a C-terminal group and/or a side chain group. Preferred are N- and/or C-terminal modifications.

Hence, the present invention also relates to derivatives of the monomeric and multimeric peptidic compounds obtained from at least one modification, in particular peptidic derivatives selected from amidated, acetylated, sulfated, lipidated, phosphorylated, glycosylated, oxidized or polyethylene glycol-modified derivatives.

An especially preferred modification is the attachment of at least one lipid moiety, which is at least one amino carboxylic acid comprising a linear or cyclic, saturated or mono- or polyunsaturated hydrocarbon group having 3 to 25 and preferably 5 to 25 C-atoms, e.g. 5-amino valeric acid (5-Ava), 5-amino pentanoic acid, 8-amino octanoic acid (8-Aoa) or 2-amino decanoic acid (2-Ada). Preferably, the lipid moiety is attached to the N- and/or C-terminus of the compound. Lipid moieties may be e.g. attached to free N-termini or C-termini of peptidic compounds and/or multimeric compounds. Lipid moieties, however, may also be attached to N- and/or C-terminal linkers, e.g. as described for compounds (IIIa), (IIIb) and (IIIc). In a preferred embodiment of compounds (IIIb) and (IIIc), the C-terminal linkers $Y^2$ and $Y^3$ are trifunctional linkers to which a lipid moiety may be attached. The lipid moiety may be bond to the peptide by an amide bond.

A further preferred embodiment is the attachment of acyl, e.g. acetyl groups yo the N-termini and/or C-termini and/or the amidation of free C-termini.

The compounds of the present invention may have antipathogenic activity, in particular antiviral or/and antibacterial activity.

In particular, the peptide compounds of the invention exhibit a significant antiviral activity against a broad spectrum of viruses selected from both DNA viruses and RNA viruses. In particular, the antiviral peptide compounds of the invention can inactivate the viruses before they enter into cells, by preventing the attachment and/or adsorption of the virus to the target cell.

Examples of DNA viruses are the Parvoviridae family, including in particular Erythrovirus, the Adenoviridae family, the Papovaviridae family, including in particular Papillomavirus and Polyomavirus, the Herpesviridae family, including in particular Herpes simplex virus, Cytomegalovirus and Epstein-Barr virus, the Poxyiridae family, including in particular Variola virus and the Hepadnaviridae family, including in particular Hepatitis B virus.

Examples of RNA viruses are the Picornaviridae family, including in particular Enteroviruses (e.g. Poliovirus, Coxsackievirus B and A) and Hepatovirus (e.g. Hepatitis A virus), the Caliciviridae family, including in particular Hepatitis E virus, the Togaviridae and Flaviviridae (Arboviruses) families, including in particular Alphaviruses, Flaviviruses and Rubella viruses, the Flaviviridae family, including in particular Hepatitis C virus, the Coronaviridae family, including in particular Human coronavirus, the Paramyxoviridae family, including in particular Parainfluenza virus, Mumps virus, Morbillivirus and Respiratory syncytial virus, the Rhadoviridae family, including in particular Vesicular stomatitis virus and Rabies virus, the Filoviridae family, including in particular Marburg virus and Ebola virus, the Orthomyxoviridae family, the Arenaviridae family, including in particular Lymphocytic choriomemingitis virus and Lassa virus, the Bunyaviridae family, including in particular Rift Valley fever virus and Hantaan virus, the Reoviridae family, including in particular Mammalian reovirus, Colorado tick fever virus and Rotavirus and the Retroviridae family, including in particular HIV, Human T-cell Leukemia virus 1 (HTLV-1) and HTLV-2. Further viruses may be the Hepatitis D virus (Deltavirus). Further, the peptidic compound may be active against the Proteinaceous Infectious Particles (PRIONS).

Very preferably, the compounds of the invention have antiviral activity against the herpes viridae family, preferably herpes simplex, in particular HSV-1 and HSV-2, human cytomegalo virus (HCMV), papovaviridae family, preferably human papillomavirus (HPV) and the retroviridae family, preferably human immunodeficiency virus HIV.

In another aspect, the compounds of the invention have antibacterial activity.

In particular, the peptidic compounds are active against bacteria such as *Chlamydia trachomatis* or/and *Neisseria Gonorrhoeae*.

Consequently, the peptidic compounds of the invention show an activity in the prevention and treatment of pathogenic, in particular viral or/and bacterial infections. In a very preferred embodiment, the compounds of the invention are active against sexual infections wherein the disease is a vaginally-, rectally-, orally-transmitted infection selected from one or more of the group of herpes simplex (e.g. HSV-1 and HSV-2), cytomegalovirus (HCMV), human papilloma virus (HPV), human immunodeficiency virus (HIV), *Chlamydia trachomatis* or/and *Neisseria Gonorrhoeae*.

A further subject-matter of the present invention is a composition for medical use comprising at least one compound as defined above, e.g. a peptidic or multimeric compound as defined above, together with pharmaceutically acceptable carriers, diluents and/or adjuvants. For use in human or veterinary medicine, the composition is preferably in form of a pharmaceutical dosage form selected from solids, liquids or gels and combinations thereof, e.g. as an eyewash, mouthwash, ointment, aerosol or topical product. The pharmaceutical dosage form comprises an amount of the active agent which is effective for the treatment and/or prevention of disorders caused by, associated with or accompanied by the presence of pathogenic organisms. The actual amount of the active agent may vary depending on the administration route and the type and severity of disorder to be treated.

To achieve the desired effect(s), the peptidic monomeric or multimeric compound may be administered as single or divided dosages, for example, of at least about 0.01 mg/kg to about 200 to 550 mg/kg, of at least about 0.01 mg/kg to about 100 to 300 mg/kg, at least about 0.1 mg/kg to about 50 to 100 mg/kg or at least about 1 mg/kg to about 10 to 50 mg/kg of body weight or at least about 1 mg/kg to about 20 mg/kg of body weight, although other dosages may provide beneficial results.

To prepare the pharmaceutical composition, the peptides of the invention are synthesised or otherwise obtained, purified as necessary or desired, and then preferably lyophilised and stabilized. The peptide can then be adjusted to the suitable concentration and optionally combined with the other pharmaceutically acceptable agents.

Thus, one or more suitable unit dosage forms comprising the therapeutic peptides of the invention can be administered by a variety of routes including oral, topical, parenteral (including subcutaneous, intravenous, intramuscular and intraperitoneal), vaginal, rectal, dermal, transdermal, intrathoracic, intrapulmonary and intranasal (respiratory) routes.

For topical administration, the active agents may be formulated as is known in the art for direct application to a target area, for example nails and skin. Forms chiefly conditioned for topical application take the form, for example, of laquers, creams, milks, gels, powders, dispersion or microemulsions, lotions thickened to a greater or lesser extent, impregnated pads, ointments or sticks, aerosol formulations (e.g. sprays or foams), soaps, detergents, lotions or cakes of soap. Other conventional forms for this purpose include wound dressings, coated bandages or other polymer coverings, ointments, creams, lotions.

In a further preferred embodiment, the monomeric or multimeric compounds or the composition of the present invention are used in veterinary medicine applications.

In another aspect, the composition of the invention comprises at least one additional antipathogenic, in particular antiviral or/and antibacterial agent, wherein the agent is particularly a protease inhibitor, a polymerase inhibitor, an integrase inhibitor, an entry inhibitor, an assembly/secretion inhibitor, a translation inhibitor, an immunostimulant or any combination thereof.

Further, the present invention shall be explained in more detail by the following figures and examples.

In the context of the following figures and examples, the particularly preferred multimeric peptidic compounds of the present invention, formulae (VI) and (VII), are referred to herein as SB105 and SB105-A$_{10}$, respectively. As negative control compound, the multimeric peptidic compound referred to herein as SB104 is used. The structures of said peptic compounds are shown in table 2, wherein A is alanine, S is serine, L is leucine, R is arginine, V is valine, I is isoleucine, K is lysine, Q is glutamine and N is asparagine.

TABLE 2

| Formula | Compound name | Peptide sequence (from N- to -C) |
|---|---|---|
| VI | SB105 | (ASLRVRIKKQ)$_4$-Lys$_2$-Lys-β-Ala |
| VII | SB105-A$_{10}$ | (ASLRVRIKK)$_4$-Lys$_2$-Lys-β-Ala |
| VIII | SB104 | (NKKIRVRL)$_4$-Lys$_2$-Lys-β-Ala |

EXAMPLES

Materials

Figure 1A:
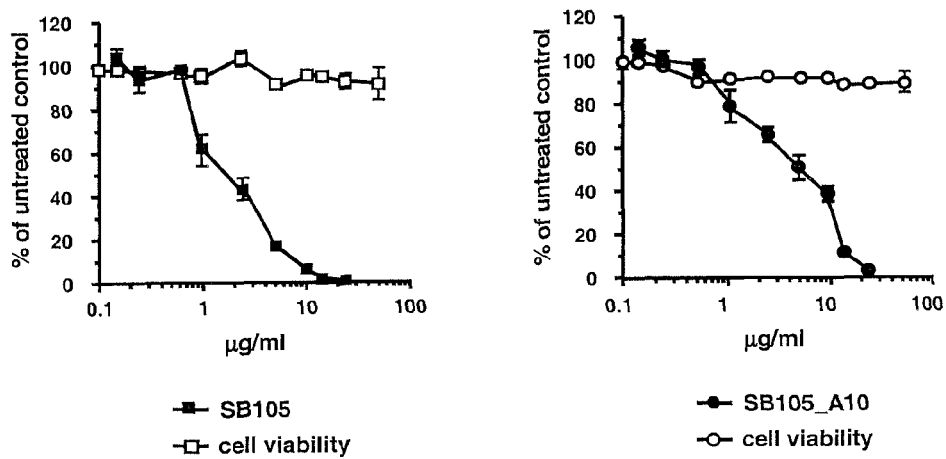
FIGS. 1A and B. Antiviral activity of the dendrimeric peptides SB105 (VI) and SB105-A$_{10}$ (VII) against HSV-1 and HSV-2. Vero cells, pretreated and treated with increasing concentrations of the SB105 or SB105-A$_{10}$ peptides 1 h prior to and during infection, were infected with HSV-1 (panel 1A) or HSV-2 (panel 1B) at a M.O.I. of 0.1, until an extensive viral cytopathic effect was observed in the untreated controls. The extent of HSV-1 and HSV-2 replication was then assessed by titrating the infectivity of supernatants of Vero suspensions by standard plaque assay. Plaques were microscopically counted, and the mean plaque counts for each peptide concentration were expressed as a percentage of the mean count of the controls. The number of plaques was plotted as a function of drug concentration, and the concentration producing a 50% reduction in plaque formation (IC$_{50}$) was determined. The data shown represent means±SD of three independent experiments (error bars).
Figure 1B:
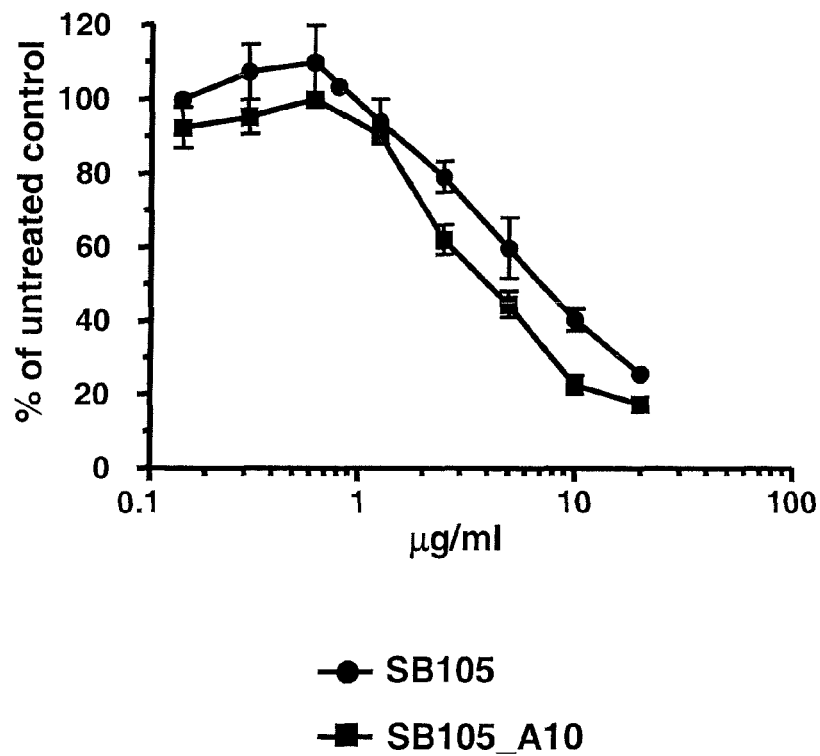

Solvents, all of HPLC grade, were obtained from Sigma Aldrich (St. Louis, Mo., US) and used without further purification. N,N-diisopropylethylamine (DIEA), piperidine, trifluoroacetic acid and triisopropylsilane were purchased from Aldrich and Fluka (St. Louis, Mo., US). Fmoc-aminoacids, HOBT, HBTU and resins were supplied from Chem-Impex International (Wooddale, Ill.) and Merck (Darmstadt, Germany).

Peptide Synthesis

All the peptides were synthesised by solid phase synthesis on a MultiSynTech Syro (Witten, Germany), using Fmoc/tBu chemistry. Coupling activation was carried out by HOBt/DIEA/HBTU (1/2/0.9) in DMF and the Fmoc-protection on amine was removed employing 40% piperidine in NMP. Side chain protecting groups were: trityl for Gln and Asn; 2,2,4,6,7-pentamethyldihydro-benzofuran-5-sulfonyl (Pbf) for Arg; tert-butyl ether for Ser; tert-butyloxycarbonyl (Boc) for Lys, Pro and Trp. Fmoc-Lys(Fmoc)-OH was the amino acid used to synthesize dimeric and tetrameric peptides. Tetrameric, dimeric and linear peptides were prepared on a Rink amide 4-benzhydrylamine (MBHA) resin, evaluating by spectrophotometric measurements the final loading in free amino groups, while acid peptides were prepared on a 2-chlorotrityl chloride resin. All peptides were cleaved from the resins and deprotected by treatment with trifluoroacetic acid, water and triisopropylsilane (95:2.5:2.5). The crude peptides, obtained by precipitation in diethyl ether, were purified by Waters HPLC-UV (Milford, Mass.) on a C$_{12}$ Phenomenex column and characterized by Bruker MALDI-TOF spectrometry (Billerica, Mass.).

Example I

Tetrameric Peptides Synthesis: Formulae (VI) (SB105), (VII) (SB105-A$_{10}$) and (VIII) (SB104)

The general procedure of peptide synthesis is reported previously. After synthesis, the crude peptides were purified by HPLC-UV and characterized by MALDI-TOF. The purity grade determined by HPLC-UV is >90%.

In particular, masses values (M+H) obtained are: Formula (VI) calcd is 5194.5 (M), found is 5195.5 (M+H); Formula (VII) calcd 4681.9 is (M), found is 4682.9 (M+H); Formula (VIII) calcd 4506.0 is (M), found is 4507.1 (M+H);

Example II

Antiviral Activity of SB105 and SB105-A$_{10}$ Peptides Against HSV-1 and HSV-2

The effects of SB105 and SB105-A$_{10}$ dendrimeric peptides on the in vitro productive replication of HSV-1 and HSV-2 were analyzed by a virus yield reduction assay. To this purpose, African green monkey fibroblasts (Vero) seeded at a density of $5\times10^4$/well in 24-well plates were incubated in duplicate at 37° C. with different concentrations of SB105 (Formula VI) or SB105-A$_{10}$ (Formula VII) peptides dissolved in culture medium or left untreated. After 1 hour, cells were infected with HSV-1 or HSV-2 at a M.O.I. of 0.1 PFU/cell. Following virus adsorption (2 h at 37° C.), cultures were maintained in medium containing the corresponding peptide (pre- and post-treatment), and incubated until control cultures displayed extensive cytopathic effect (48 h p.i.). The cells and supernatants from the antiviral assay were then harvested and disrupted by sonication. The extent of virus replication was assessed by titrating the infectivity of supernatants from cell lysates in duplicate by standard plaque assay on Vero cells. To determine cell viability, Vero cells were exposed to increasing concentrations of peptides. After 6 days incubation, the number of viable cells was determined by the 3-(4,5-dimethylthiazol-2-yl)-2,5-diphenyltetrazolium bromide (MTT) method, as previously described (Pauwels et al., 1988).

To assess the effect of SB105 and SB105-A$_{10}$ on HSV-1 and HSV-2 entry into target cells, entry assays were performed essentially as described by MacLean (1988) and with the modifications introduced by Shogan et al. (2006). Briefly, Vero cells seeded at a density of $5\times10^4$/well in 24-well plates, were prechilled to 4° C. and infected with 200 PFU of HSV-1 or HSV-2 for 3 h at 4° C. to allow virus attachment. Cells were then washed with cold phosphate-buffered saline (PBS) three times to remove unadsorbed viruses. Then to assay the effect of dendrimeric peptides on virus entry, different concentrations of SB105, SB105-A$_{10}$, SB104 (as negative control for inhibition of viral replication) or heparin (as a positive control for inhibition of viral adsorption) were added to the cells, and the temperature was shifted to 37° C. for 2 h prior inactivation of extracellular viruses. To inactivate extracellular viruses (and remove any test compounds in the entry assay) cells were incubated with 1 ml of 100 mM glycine-140 mM NaCl, pH 3.0 for 60 s at room temperature. Cells were then washed with PBS three times to return the pH to neutral value, and overlaid with medium containing 1.2% methylcellulose, and incubated at 37° C. Forty eight hours later, plates were fixed and stained with crystal violet and the viral plaques counted. In parallel, the same amount of viruses were allowed to attach to cells for 3 h at 4° C. as above, and cells were overlaid with methylcellulose containing medium The number of plaques produced by these untreated cell monolayers was set at 100%.

Figure 2:
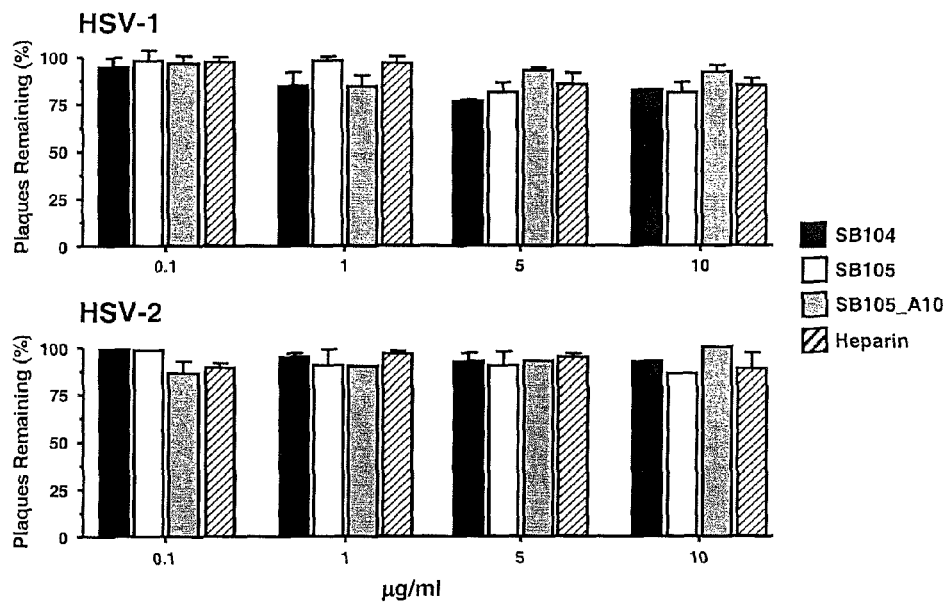
FIG. 2. Treatment with SB105 and SB105-A$_{10}$ dendrimeric peptides after viral adsorption do not affect HSV-1 and HSV-2 entry into Vero cells. Pre-chilled Vero cell monolayers were infected with 200 PFU of HSV-1 or HSV-2 for 3 h at 4° C., washed and incubated with different concentrations of SB105, SB105-A$_{10}$, SB104 or heparin at to 37° C. for 2 h prior inactivation of extracellular viruses. Cells were then overlaid with medium containing 1.2% methylcellulose, and incubated at 37° C. After 48 h, viral plaques were counted, and the mean plaque counts for each compound concentration expressed as a percentage of the mean count of the untreated controls. The data shown represent means±SD of three independent experiments (error bars).

FIG. 2 shows that incubation of peptides after virus adsorption did not affect the viral entry into target cells.

Figure 3:
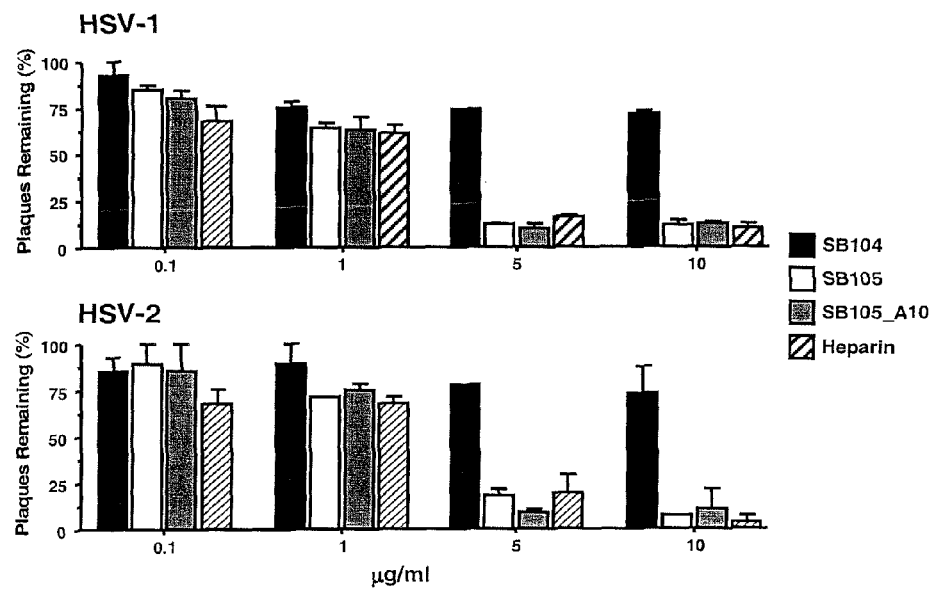
FIG. 3. The dendrimeric peptides SB105 and SB105-A$_{10}$ inhibit HSV-1 and HSV-2 attachment to Vero cells. Pre-chilled Vero cells were incubated at 4° C. with different concentrations of SB105, SB105-A$_{10}$, SB104 or heparin and with 200 PFU of HSV-1 or HSV-2. Following virus adsorption (3 h at 4° C.), cells were then washed with cold PBS three times to remove compound and unadsorbed viruses, overlaid with medium containing 1.2% methylcellulose and incubated at 37° C. for 48 h. Viral plaques were then stained and counted and the mean plaque counts for each peptide concentration expressed as a percentage of the mean count of the controls. The data shown represent means±SD of three independent experiments (error bars).

To test whether the SB105 and SB105-A$_{10}$ peptides act at the viral adsorption stage (MacLean, 1988; Shogan et al., 2006), Vero cells seeded at a density of $5\times10^4$/well in 24-well plates, were prechilled to 4° C. and incubated in duplicate at 4° C. with different concentrations of SB105, SB105-A$_{10}$, SB104 (as negative control for inhibition of viral replication) or heparin (as a positive control for inhibition of viral adsorption) and with 200 PFU of HSV-1 or HSV-2. Following virus adsorption (3 h at 4° C., a condition that is known to allow virus adsorption only), cells were then washed with cold PBS three times to remove compound and unadsorbed viruses, overlaid with medium containing 1.2% methylcellulose and incubated at 37° C. Forty eight hours later, plates were fixed and stained with crystal violet and the viral plaques counted. As shown in FIG. 3, SB105 and SB105-A$_{10}$ peptides prevented attachment of both HSV-1 and HSV-2 to Vero cells in a concentration-dependent manner. As expected, heparin treatment prevented virus adsorption. In contrast, SB104 did not significantly reduce the binding of HSV-1 and HSV-2 virions to Vero cells. Thus, these results indicate that SB105 and SB105-$A_{10}$ inhibit the HSV-1 and HSV-2 adsorption to the target cells.

Example III

Antiviral Activity of SB105 and SB105-$A_{10}$ Peptides Against HCMV

The virus yield reduction assay was employed to investigate the inhibitory activity of SB105 and SB105-$A_{10}$ dendrimeric peptides on the in vitro replication of HCMV (Luganini et al., 2008). To this purpose, low-passage human embryonic lung fibroblasts (HELFs) seeded at a density of 5×10$^4$/well in 24-well plates, cells were incubated in duplicate at 37° C. with different concentrations of SB105 or SB105-$A_{10}$ peptides dissolved in culture medium or left untreated. After 1 hour, they were infected with HCMV AD169 or HCMV AL1 at a M.O.I. of 1 PFU/cell. Following virus adsorption (2 h at 37° C.), cultures were maintained in medium containing the corresponding peptide, and then incubated until control cultures displayed extensive cytopathic effect (6 days p.i.). The cells and supernatants from the antiviral assay were then harvested and disrupted by sonication. The extent of virus replication was assessed by titrating the infectivity of supernatants of cell suspensions by standard plaque assay on HELFs.

To evaluate the effects of SB105 and SB105-$A_{10}$ dendrimeric peptides on the in vitro replication of the endotheliotropic HCMV VR1814 strain, low-passage (two to six) human umbilical vein endothelial cells (HUVECs) obtained by trypsin treatment of umbilical cord veins were seeded at a density of 5×10$^4$/well in 24-well plates. After 24 h, cells were incubated in duplicate at 37° C. with different concentrations of SB105 or SB105-$A_{10}$ peptides, dissolved in culture medium or left untreated. One hour later, they were infected with HCMV VR1814 at a M.O.I. of 1 PFU/cell. Following virus adsorption (2 h at 37° C.), cultures were maintained in medium containing the corresponding peptide, and incubated until control cultures displayed extensive cytopathic effect (6 days p.i.). The cells and supernatants from the antiviral assay were then harvested and disrupted by sonication. The extent of virus replication was assessed by titrating the infectivity of supernatants from cell lysates by the indirect immunoperoxidase staining procedure on HUVECs using a monoclonal antibody (mAb) reactive to the HCMV IE1 and IE2 proteins (clone E13; Argene Biosoft) (Revello et al., 2001).

To determine cell viability, HELFs or HUVECs were exposed to increasing concentrations of peptides. After 6 days of incubation, the number of viable cells was determined by the 3-(4,5-dimethylthiazol-2-yl)-2,5-diphenyltetrazolium bromide (MTT) method, as previously described (Pauwels et al., 1988).

Figure 4A:
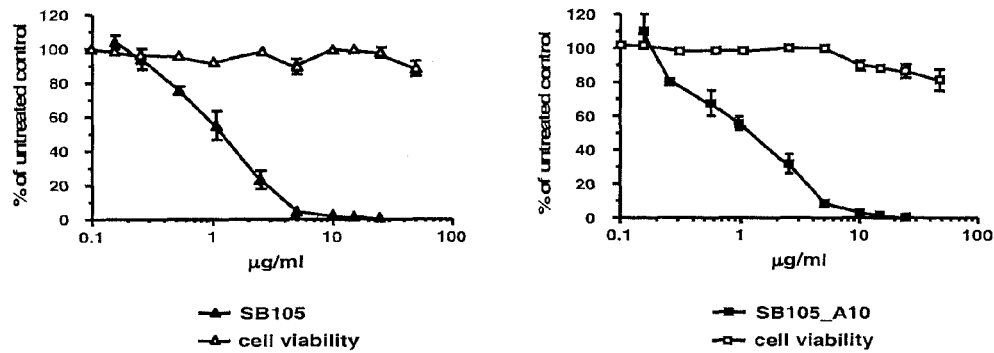
FIGS. 4A and 4B. HCMV replication is inhibited by the dendrimeric peptides SB105 and SB105-A$_{10}$. HELFs were infected with the HCMV laboratory strain AD169 (FIG. 4A) or with clinical HCMV isolate AL1 (FIG. 4B) at a M.O.I. of 1, and, where indicated, the cells were pretreated and treated with increasing concentrations of the different peptides 1 h prior to and during infection, until an extensive viral cytopathic effect was observed in the untreated controls. HUVECs were infected with the endotheliotropic and clinical HCMV isolate VR1814 (FIG. 4B) at a M.O.I of 1. The extent of AD169 or AU replication was then assessed by titrating the infectivity of supernatants of HELF suspensions by standard plaque assay. The extent of VR1814 replication was measured by titrating the infectivity of supernatants of cell suspensions by the indirect immunoperoxidase staining procedure on HUVECs using a monoclonal antibody (mAb) reactive to the HCMV IE proteins. Plaques were microscopically counted, and the mean plaque counts for each peptide concentration were expressed as a percentage of the mean count of the controls. The number of plaques was plotted as a function of drug concentration, and the concentration producing a 50% reduction in plaque formation (IC$_{50}$) was determined. The data shown represent means±SD of three independent experiments (error bars).
Figure 4B:
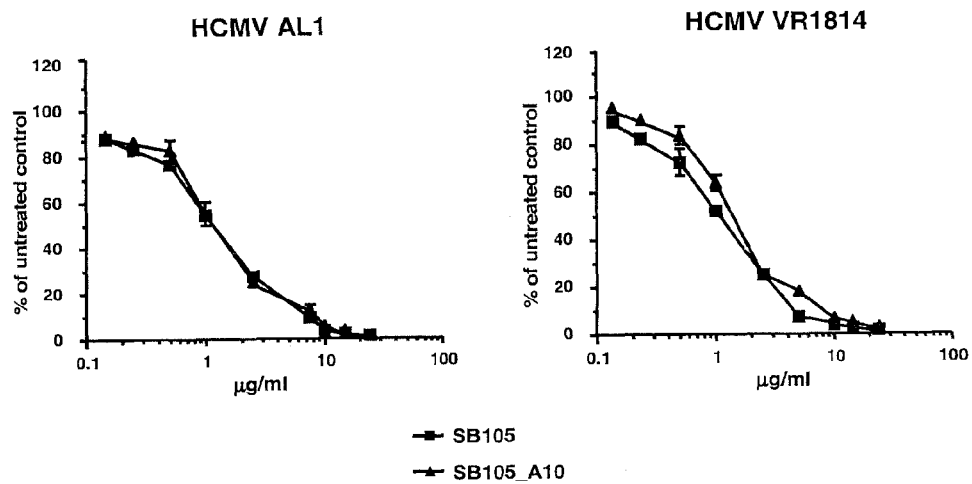

As shown in FIG. 4A, pretreatment of HELFs with SB105 and SB105-$A_{10}$ peptides 1 h before infection caused a significant concentration-dependent inhibitory effect on the in vitro replication of the HCMV laboratory strain AD169 at 6 days p.i. The concentrations of SB105 and SB105-$A_{10}$ that resulted in 50% inhibition of HCMV AD169 replication ($IC_{50}$) were of 1.17 and 1.36 µg/ml, respectively. The inhibitory effect of SB105 and SB105-$A_{10}$ was neither virus-strain- nor cell-type-specific (FIG. 4B), because it was also observed in HELFs infected with the clinical isolates AL1 (a clinical isolate recovered from a bronchoalveolar lavage fluid of a lung transplant recipient) ($IC_{50}$ of 1.2 µg/ml for SB105 and SB105-$A_{10}$) or in HUVECs infected with the endotheliotropic VR1814 strain (a clinical isolates recovered from a cervical swab from a pregnant woman and adapted to the growth in endothelial cells) (Revello et al., 2001) ($IC_{50}$ of 1.1 and 1.3 µg/ml for SB105 and SB105-$A_{10}$, respectively).

Worthy of note, none of the peptides analyzed significantly affected the viability of HELFs and HUVECs in the relevant range of concentrations, since >90% of cells were viable after 6 days treatment with peptides up to a concentration of 50 µg/ml (FIG. 4A), demonstrating that the antiviral activity against HCMV was not due to cytotoxicity of the target cells themselves.

To investigate the effect of SB105 and SB105-$A_{10}$ on HCMV entry into target cells, HELF cells seeded a density of 5×10$^4$/well in 24-well plates, were prechilled to 4° C. and infected with 200 PFU of HCMV AD169 for 3 h at 4° C. to allow for viral attachment. Cells were then washed with cold phosphate-buffered saline (PBS) three times to remove unadsorbed viruses. To assay the effect of dendrimeric peptides on entry, different concentrations of SB105, SB105-$A_{10}$, SB104 (as negative control for inhibition of viral replication) or heparin (as a positive control for inhibition of viral adsorption) were added to the cells, and the temperature was shifted to 37° C. for 2 h prior inactivation of extracellular viruses. To inactivate extracellular viruses (and remove any test compounds in the entry assay) cells were incubated with 1 ml of 100 mM glycine-140 mM NaCl, pH 3.0 for 60 s at room temperature. Cells were then washed with PBS three times to return the pH to neutral, overlaid with medium containing 1.2% methylcellulose, and incubated at 37° C. After 6 days, plates were fixed and stained with crystal violet and the viral plaques counted. In parallel, the same amount of HCMV was allowed to attach to cells for 3 h at 4° C. as above, and cells were overlaid with methylcellulose containing medium, an the number of plaques produced by these untreated cell monolayers was set at 100%.

Figure 5:
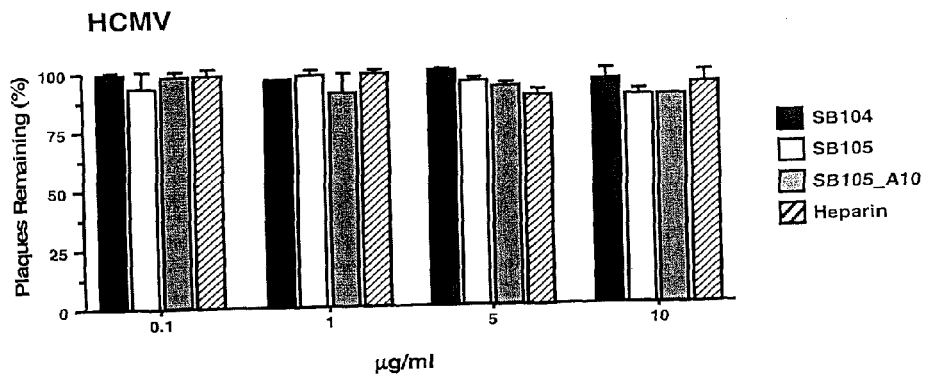
FIG. 5. Treatment with SB105 and SB105-A$_{10}$ dendrimeric peptides after viral adsorption do not affect HCMV entry into HELF cells. Pre-chilled HELF cell monolayers were infected with 200 PFU of HCMV AD169 for 3 h at 4° C., washed and incubated with different concentrations of SB105, SB105-A$_{10}$, SB104 or heparin at to 37° C. for 2 h prior inactivation of extracellular viruses. Cells were then, overlaid with medium containing 1.2% methylcellulose, and incubated at 37° C. for 6 days. Thereafter, viral plaques were counted, and the mean plaque counts for each compound concentration were expressed as a percentage of the mean count of the untreated controls. The data shown represent means±SD of three independent experiments (error bars).

FIG. 5 shows that incubation of peptides after virus adsorption did not affect the viral entry into target cells.

Figure 6:
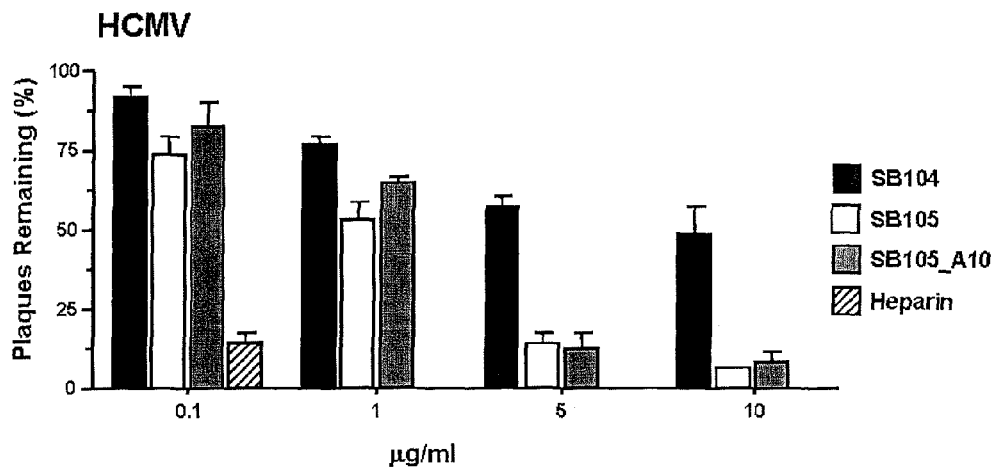
FIG. 6. HCMV adsorption to target cells is inhibited by SB105 and SB105-A$_{10}$ dendrimeric peptides. Pre-chilled HELF cells were incubated at 4° C. with different concentrations of SB105, SB105-A$_{10}$, SB104 or heparin and with 200 PFU of HCMV AD169. Following virus adsorption (3 h at 4° C.), cells were washed with cold PBS three times to remove compound and unadsorbed viruses, overlaid with medium containing 1.2% methylcellulose and incubated at 37° C. for 6 days. Viral plaques were then stained and counted and the mean plaque counts for each peptide concentration were expressed as a percentage of the mean count of the controls. The data shown represent means±SD of three independent experiments (error bars).

To test whether the SB105 and SB105-$A_{10}$ peptides can interfere with HCMV attachment to the target cells, HELF cells were seeded a density of 5×10$^4$/well in 24-well plates. After 24 h, they were prechilled to 4° C. and incubated in duplicate at 4° C. with different concentrations of SB105, SB105_$A_{10}$, SB104 (as negative control for inhibition of viral replication) or heparin (as a positive control for inhibition of viral adsorption) and with 200 PFU of HCMV AD169. Following virus adsorption (3 h at 4° C., a condition that is known to allow virus adsorption only), cells were then washed with cold PBS three times to remove compound and unadsorbed viruses, overlaid with medium containing 1.2% methylcellulose and incubated at 37° C. for 6 days. Plates were then fixed and stained with crystal violet and the viral plaques counted. As shown in FIG. 6, SB105 and SB105_$A_{10}$ peptides potently inhibited the attachment of HCMV to HELF cells in a concentration-dependent manner. As expected, heparin treatment prevented virus adsorption. In contrast, SB104 did not significantly reduce the adsorption of HCMV virions to HELF cells. Taken together, these results demonstrate that SB105 and SB105_$A_{10}$ inhibit the replication of HCMV by preventing the attachment of the virus to the target cells.

Example IV

Activity Against Human Papilloma Virus

Cell Culture

The 293TT cell line derived from human embryonal kidney cells transformed with the SV40 large T antigen was cultured in Dulbecco's modified Eagle's medium (DMEM)

(Gibco/BRL, Gaithersburg, Md., USA) supplemented with heat-inactivated 10% bovine serum (Gibco/BRL), Glutamax-I (Invitrogen, Carlsbad, Calif., USA) and nonessential aminoacids. This cell line allows high levels of protein to be expressed from vectors containing the SV40 origin due to overreplication of the expression plasmid (Buck et al., 2004).

Pseudovirion Production

HPV-16 PsV were produced according to previously described methods (Buck et al., 2005). Briefly, 293TT cells were transfected with the plasmid p16sheLL expressing the papillomavirus major and minor capsid proteins (L1 and L2) together with a reporter plasmid expressing the secreted alkaline phosphatase (SEAP) or the green fluorescence protein (GFP) named pYSEAP or pfwB respectively. Capsids were allowed to mature overnight in cell lysate; the clarified supernatant was then loaded on top of a 27-33-39% Optiprep (Sigma-Aldrich, St. Louis, Mo., USA) density gradient at room temperature for 4 h. The material was centrifuged at 234000×g for 3.30 h at 16° C. in an SW50.1 rotor (Beckman Coulter, Inc. Fullerton, Calif., USA) and collected by bottom puncture of the tubes. Fractions were inspected for purity on 10% SDS-Tris-glycine gels, titrated on 293TT cells to test for infectivity by SEAP or GFP detection, then pooled and frozen at −80° C. until needed. The L1 protein content of PsV stocks was determined by comparison with bovine serum albumin standards in Coomassie-stained SDS-PAGE gels.

Inhibition Assays

For the Secreted Embryonic Alkaline Phosphate (SEAP)-based assays 293TT cells were preplated 3-4 h in advance in 96-well tissue culture-treated flat bottom plates at a density of 30,000 cells/well in 100 µl neutralization buffer (DMEM without phenol red, 10% heat-inactivated FBS, 1% glutamate, 1% nonessential amino acids, 1% penicillin-streptomycin-fungizone, and 10 mM HEPES). To generate dose-response curves, diluted PsV stocks (80 µl/well) were placed on 96-well nontreated sterile, polystyrene plates (Nalge-Nunc, Roskilde, Denmark), combined with 20 µl of serially diluted peptides, and placed on ice for 1 h. The 100-µl PsV-compounds mixture was transferred onto the preplated cells and incubated for 68-72 h. The final concentration of PsV was approximately 1 ng/ml L1. After incubation, 50 µl of supernatant were harvested and clarified at 1500×g for 5 min. The SEAP content in the clarified supernatant was determined using a Great ESCAPE SEAP Chemiluminescence Kit (BD Clontech, Mountain View, Calif., USA) as directed by the manufacturer. Ten minutes after the substrate was added, samples were read using a Lumino luminometer (Stratec Biomedical System, Birkenfeld, Germany).

The 50% inhibition concentration ($IC_{50}$) values were determined using Prism (GraphPad Software, San Diego, Calif., USA).

The Green Fluorescent Protein (GFP)-based assays were performed as described above. The GFP-positive cells were counted under a fluorescence microscope and the percentage of infection calculated by comparison of treated and untreated cells.

Cell Viability Assay

Cells were seeded at a density of $5 \times 10^4$/well in 24-well plates; the next day they were treated with serially diluted peptides to generate dose-response curves. Forty-eight or 72 h after treatment, cell viability was determined by the 3-(4,5-dimethylthiazol-2-yl)-2,5-diphenyltetrazolium bromide (MTT) method; 50% cytotoxic concentration ($CC_{50}$) values were determined using Prism.

Electron Microscopy

An aliquot of diluted HPV-PsV preparations was placed on a grid and air dried prior to examination. Microscopy was performed using a Philips CM10 transmission electron microscope; micrographs were taken of random sections at different powers of magnifications.

Characterization of Purified HPV-16 PsV

Figure 7:
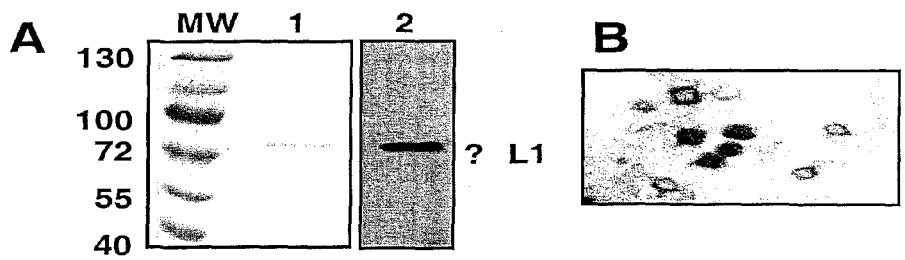
FIG. 7. Characterization of purified HPV-16-SEAP PsV. (A) An aliquot of purified PsV preparation was analyzed by SDS-PAGE with Coomassie Brilliant Blue staining (Lane 1) or immunoblotting (Lane 2) with an anti-L1 antibody (B0580 Dako Corporation, Carpinteria, Calif., USA). (B) Electron micrograph of a purified PV preparation.

HPV-16 was chosen as a model since it is the most oncogenic genital HPV type (Lowy and Howley, 2001). To check the quality of the HPV-16-SEAP PsV preparation used in the subsequent assays, an aliquot was subjected to SDS-PAGE. As shown in FIG. 7A, a major band migrating at 55 kD was detected by Coomassie Brilliant Blue staining (lane 1) and was confirmed to be the L1 major capsid protein by Western blotting (lane 2). No L1-reactive proteolytic degradation products were observed at molecular weights below 55 kD, indicating the good quality of the preparation. FIG. 7B shows an electron micrograph of the same PsV stock. PsV routinely exhibited an average diameter of 50-60 nm, which is similar to that of an authentic HPV capsid, and appeared as individual, well-defined particles with minimal aggregation.

Inhibitory Effect of Synthetic Peptides Against HPV-PsV Infection.

The early events of a PsV infection resemble those of a natural HPV infection since the PsV consists of a reporter plasmid encapsidated by a capsid composed of the two viral capsid proteins (L1 and L2) like an authentic HPV capsid. After PsV binding to and entry into the cell, the reporter plasmid is transported to the nucleus for expression of the reporter gene (Buck et al., 2004). We exploited a PsV-based assay to screen a panel of synthetic peptides as antagonists of HPV-16 infection. To generate dose-response curves, serial dilutions of peptides were preincubated with aliquots of HPV-16-SEAP PsV and then added to 293TT cell cultures. Inhibition of PsV-mediated delivery of the SEAP reporter plasmid 72 h post-infection was measured by chemiluminescence analysis of the cell supernatants. As shown in Table 3, the synthetic peptide SB105-$A_{10}$ turned out to be the most active. It strongly inhibited the HPV-16-SEAP PsV infection at 50% inhibitory concentrations ($IC_{50}$) of 2.8 µg/ml. The $CC_{50}$ were >100 µg/ml for all compounds tested, indicating that the inhibitory activity was not a consequence of cytotoxicity. Similar results were obtained when GFP-based assays were used.

TABLE 3

Inhibitory activity of synthetic peptides against HPV-16 PsV

| Formula | Peptide name | $IC_{50}$* | $CC_{50}$* |
|---|---|---|---|
| VI | SB105 | 11.6 | >100 |
| VII | SB105-$A_{10}$ | 2.8 | >100 |

*All values are given in µg/ml

Example V

Activity Against Human Immunodeficiency Virus

Antiviral Activity of SB105-$A_{10}$ Peptide Against HIV.

In order to evaluate the antiviral activity of SB105_A10 against HIV-1, the HIV-1 RNA viral load and HIV-1 gag p24 content in supernatants of C8166 T lymphoblastoid cell cultures infected by T-tropic HIV-$1_{IIIb}$ strain were determined.

HIV-$1_{IIIb}$ (300 pg p24/ml) was pre-incubated for 60 minutes at 37° C. with scalar concentrations (0.1, 1, 5, 10, 20 µg/ml) of SB105-$A_{10}$ or SB104 and then added to C8166 cells, adjusted to a final density of $1\times10^6$ cells/ml, for 120 minutes at 37° C. After four washes in PBS, the cells were seeded at $5\times10^5$ cells/ml in RPMI 1640 (Gibco, Paisley, UK) plus 10% FCS (Gibco) with scalar concentrations of SB105-$A_{10}$ or SB104. Half of the medium was replaced with fresh medium at day 4 post-infection without SB105-$A_{10}$ or SB104.

Figure 8:
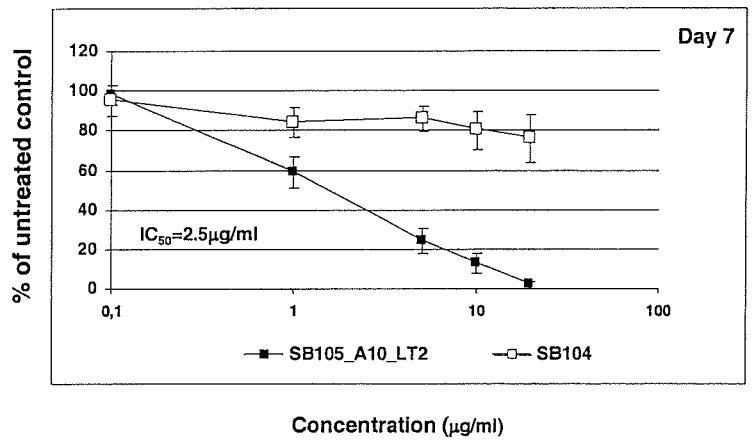
FIG. 8: Quantitative real time RT-PCR analysis of HIV-1 RNA load in HIV-1 infected C8166 cell culture supernatants at day 7 post infection. The data of SB105-A$_{10}$ or SB104-treated infected samples were expressed as percentage of untreated infected control value (100%). The data are reported as means±SD of three independent experiments performed in duplicate.
Figure 9:
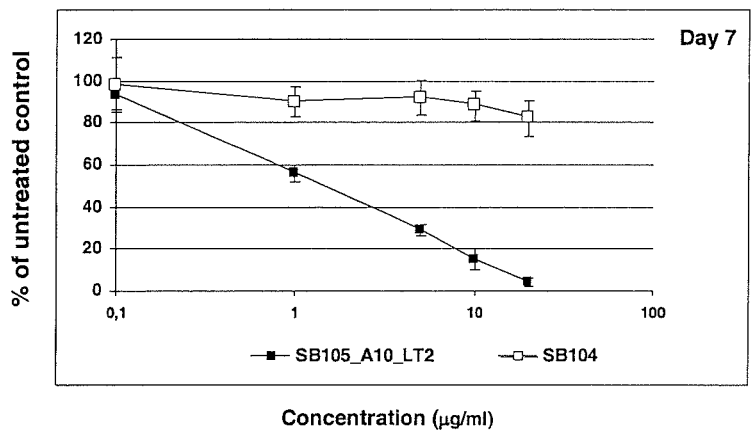
FIG. 9: ELISA HIV-1 p24 protein analysis in HIV-1 infected C8166 cell culture supernatants at day 7 post infection. The data of SB105-A$_{10}$ or SB104 treated infected samples were expressed as percentage of untreated infected control value (100%). The data are reported as means±SD of three independent experiments performed in duplicate.
Figure 10:
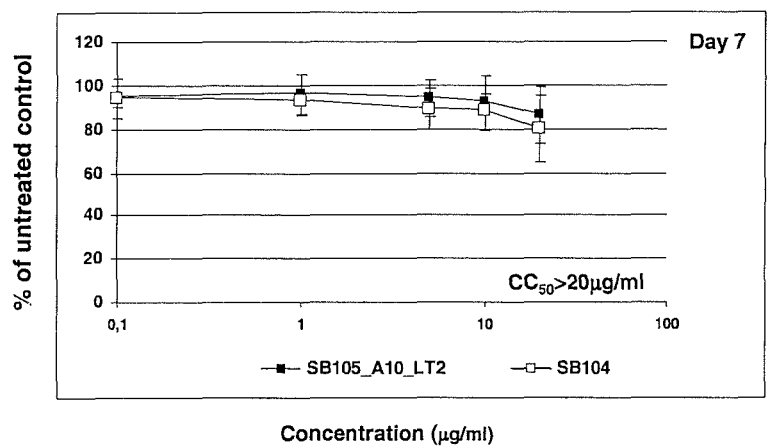
FIG. 10: C8166 cell viability determination by Trypan blue exclusion technique. Uninfected C8166 cells were left untreated or treated by scalar concentrations of SB105-A$_{10}$ or SB104. The analysis was carried out by Trypan blue exclusion technique at day 7. The data of SB105-A$_{10}$ or SB104-treated samples were expressed as percentage of untreated control value (100%). The data are reported as means±SD of three independent experiments performed in duplicate.

HIV-1 RNA viral load and HIV-1 gag p24 content were determined at day 7 post-infection in the culture supernatants in three independent experiments performed in duplicate. HIV-1 RNA was extracted by Roche high pure viral nucleic acid kit (Roche, Mannheim, Germany) from 200 µl of culture supernatants and then RNA load was assessed by quantitative real time RT-PCR as previously described (Gibellini et al., 2004). In parallel, HIV-1 gag p24 protein amount was determined by ELISA HIV-1 p24 antigen kit (Biomerieux Marcy L'Etoile, France). SB105-$A_{10}$ treatment significantly decreased both HIV-1 RNA load and HIV-1 p24 content whereas SB104 did not induce significant inhibition of HIV-1 replication activity (FIGS. 8 and 9). The concentration of SB105-$A_{10}$ causing 50% inhibition of HIV-$1_{IIIb}$ replication ($IC_{50}$) was 2.5 µg/ml. Since the antiretroviral activity may be related to possible cell toxicity of the tested compounds, we analyzed the cell viability by Trypan blue exclusion technique demonstrating that SB105-$A_{10}$ did not significantly affect cell survival (FIG. 10). Altogether these results demonstrated that HIV-$1_{IIIb}$ replication was significantly impaired by SB105-$A_{10}$ under these experimental conditions and then this molecule might be considered as a new antiretroviral drug.

REFERENCES

Bosch F. X., and de Sanjose S. 2003. Chapter 1, Human papillomavirus and cervical cancer—burden and assessment of causality. J. Natl. Cancer Inst. Monogr. 31:3-13.

Bourne N., Stanberry L. R., Kern E. R., Holan G., Matthews B., and Bernstein D. I. 2000. Dendrimers, a New Class of Candidate Topical Microbicides with Activity against Herpes Simplex Virus Infection. 44: 2471-2474.

Buck C. B., Pastrana D. V., Lowy D. R., and Schiller J. T. 2005. Generation of HPV pseudovirions using transfection and their use in neutralization assays. Methods Mol. Med. 119:445-462.

Buck C. B., Thompson C. D., Roberts J. N., Muller M., Lowy D. R., and Schiller J. T. 2006. Carrageenan is a potent inhibitor of papillomavirus infection. PLoS Pathog. 2:e69.

Buck C. B., Pastrana D. V., Lowy D. R., and Schiller J. T. 2004. Efficient intracellular assembly of papillomaviral vectors. J. Virol. 78:751-757.

Garland S. M., Hernandez-Avila M., Wheeler C. M., Perez G., Harper D. M., Leodolter S., Tang G. W., Ferris D. G., Steben M., Bryan J., Taddeo F. J., Railkar R., Esser M. T., Sings H. L., Nelson M., Boslego J., Sattler C., Barr E., and Koutsky L. A. 2007. Females United to Unilaterally Reduce Endo/Ectocervical Disease (FUTURE) I Investigators. Quadrivalent vaccine against human papillomavirus to prevent anogenital diseases. N. Engl. J. Med. 356: 1928-1943.

Garner J. A. 2003. Herpes simplex virion entry into and intracellular transport within mammalian cells. Advanced Drug Delivery Reviews. 55:1497-1513.

Gibellini D., Vitone F., Gori E., La Placa M., and Re M. C. 2004. Quantitative detection of human immunodeficiency virus type 1 (HIV-1) viral load by SYBR green real-time RT-PCR technique in HIV-1 seropositive patients. J. Virol. Meth. 115:183-189.

Giuliani, A., Pirri G., and Nicoletto S. F. 2007. Antimicrobial peptides: an overview of a promising class of therapeutics. CEJB 2:1-33

Howley P. M., and Lowy D. R. 2001. Papillomaviruses and their replication, p. 2197-2229. In B. N. Fields, D. M. Knipe, and P. M. Howley (ed.), Fields Virology, Lippincott-Raven, Philadelphia, Pa.

Landolfo S., Gariglio M., Gribaudo G., and Lembo D. 2003. The human cytomegalovirus. Pharmacol. Ther. 98:269-297.

Langeland N., Moore L., Holmsen H., and Haar L. 1988. Interaction of polylysine with the cellular receptor for herpes simplex virus type 1. J. Gen. Virol. 69:1137-1145

Lowy D. R., and Howley P. M. 2001. Papillomaviruses, p. 2231-2264. In B. N. Fields, D. M. Knipe, and P. M. Howley (ed.), Fields Virology, Lippincott-Raven, Philadelphia, Pa.

Luganini A., Caposio P., Landolfo S., and Gribaudo G. 2008. Phosphorothioate-modified oligodeoxynucleotides inhibit human cytomegalovirus replication by blocking virus entry. Antimicrob. Agents Chemother. 52:1111-1120.

Manhart L. E., and Koutsky L. A. 2002. Do condoms prevent genital HPV infection, external genital warts, or cervical neoplasia? A meta-analysis. Sex. Transm. Dis. 29:725-735.

Marsden M. D., and Zack J. A. 2009. Eradication of HIV: current challenges and new directions. J. Antimicrob. Chemother. 63:7-10.

McLean, A. R. 1988. HSV entry and spread. In Herpes simplex virus protocols. S. M. Brown and A. R. MacLean (Eds). Humana Press, Totowa, N.J.

Niederhafner P., Sebestik J., and Jezek J. 2005. Peptide Dendrimers. J. Peptide Sci. 11:757-788.

Pauwels R., Balzarini J., Baba M., Snoeck R., Schols D., Hederwijin P., Desmyter J., and De Clerq E. 1988. Rapid and automated tetrazolium-based colorimetric assay for the detection of anti HIV compounds. J. Virol. Methods. 20:309-321.

Quinn T. C. 2008. HIV epidemiology and the effects of antiviral therapy on long-term consequences. AIDS. 22:S7-12.

Revello M. G, Baldanti F., Percivalle E., Saracini A., De-Giuli L., Genini E., Lilleri D., Labò N., and Gerna G. 2001. In vitro selection of human cytomegalovirus variants unable to transfer virus and virus products from infected cells to polymorphonuclear leukocytes and to grow in endothelial cells. J. Gen. Virol. 82:1429-1438.

Shogan B., Kruse L., Mulamba G. B., Hu A., and Coen D. 2006. Virucidal activity of a GT-rich oligonucleotide against herpes simplex virus mediated by glycoprotein. B. J. Virol. 80:4740-4747.

Yang D., Biragyn A., Kwak L. W., and J. J. Oppenheim J. J. 2002. Mammalian defensins in immunity: more than just microbicidal. Trends Immunol. 23: 291-296.

Wilson L. E., and Gallant J. E. 2009. HIV/AIDS: the management of treatment-experienced HIV-infected patients: new drugs and drug combinations. Clin. Infect. Dis. 48:214-221.

The invention claimed is:

1. A peptidic compound having a length of up to 35 amino acid residues comprising an amino acid sequence represented by the general formula (II):

A-S-L-R-V-R-I-K-[K]$_n$-[Q]$_m$ wherein

R is an amino acid residue with an arginine side chain or an N-alkyl substituted guanidine side chain, particularly L-arginine, V and I are amino acid residues independently selected from:
(i) an amino acid residue, which has a linear straight-chain saturated or unsaturated side chain with at least three C-atoms, preferably with 3-10 C-atoms, particularly norleucine, 2-aminopentanoic acid, 2-aminooctanoic, 2-aminodecanoic acid or 2-aminododecanoic acid,
(ii) an amino acid residue, which has a branched saturated or unsaturated side chain with at least three C-atoms, preferably with 3-10 C-atoms, particularly tert-leucine, 5-methyl norleucine or homoisoleucine (4-methyl norleucine); and
(iii) an amino acid residue, which has a cyclic saturated or unsaturated side-chain with at least 3 C-atoms, preferably with 3-10 C-atoms, which is particularly selected from cyclic residues with 3-6 ring atoms, optionally comprising a C=C double bond such as cyclopropyl, cyclobutyl, cyclobutenyl, cyclopentyl, cyclopentenyl, cyclohexyl, cyclohexenyl, optionally substituted in any ring positions with aliphatic groups, preferably aliphatic groups having 1-10 C-atoms, more preferably 1-8 C-atoms, even more preferably 1-6 C-atoms and particularly preferably methyl, ethyl, isopropyl, n-propyl, n-butyl, isobutyl, such as norfuranomycin, carbafuranomycin, cyclopentylglycine, cyclopentenyl-glycine or cyclohexenylglycine, or
V is an amino acid residue with a valine side chain, and/or I is an amino acid residue with an isoleucine side chain, K is an amino acid residue with a lysine side chain, particularly L-lysine, or another amino acid residue with a positively charged side chain, particularly ornithine or 2,4-diaminobutyric acid;

Q is an amino acid residue with a glutamine side chain, particularly, L-glutamine, A is an amino acid residue with an alanine side chain, particularly L-alanine, S is an amino acid residue with a hydroxyl-substituted aliphatic or aromatic side chain, particularly an amino acid residue with a serine side chain, more particularly L-serine, L is an amino acid residue selected from
(i) an amino acid residue with a leucine side chain, particularly L-leucine,
(ii) an amino acid residue with an isoleucine side chain, particularly L-isoleucine,
(iii) an amino acid residue, which has a linear straight-chain saturated or unsaturated side chain with at least three C-atoms, preferably with 3-10 C-atoms, particularly norleucine, 2-aminopentanoic acid, 2-aminooctanoic, 2-aminodecanoic acid or 2-aminododecanoic acid,
(iv) an amino acid residue, which has a branched saturated or unsaturated side chain with at least three C-atoms, preferably with 3-10 C-atoms, particularly tert-leucine, 5-methyl norleucine or homoisoleucine (4-methyl norleucine),
(v) an amino acid residue, which has a cyclic saturated or unsaturated side-chain with at least 3 C-atoms, preferably with 3-10 C-atoms, which is particularly selected from cyclic residues with 3-6 ring atoms, optionally comprising a C=C double bond such as cyclopropyl, cyclobutyl, cyclobutenyl, cyclopentyl, cyclopentenyl, cyclohexyl, cyclohexenyl, optionally substituted in any ring positions with aliphatic groups, preferably aliphatic groups having 1-10 C-atoms, more preferably 1-8 C-atoms, even more preferably 1-6 C-atoms and particularly preferably methyl, ethyl, isopropyl, n-propyl, n-butyl, isobutyl, such as norfuranomvcin, carbafuranomvcin, cyclopentylglycine, cyclopentenyl-glycine or cyclohexenylglycine, and m and n are independently 0 or 1, and wherein the peptide compound may comprise L- and/or D-amino acid residue building blocks.

2. A peptidic compound according to claim 1, comprising an amino acid sequence selected from:

A-S-L-R-V-R-I-K-K  (IIa)

A-S-L-R-V-R-I-K-K-Q  (IIb)

wherein R, K, Q, V, I, A, L and S are defined as in claim 1.

3. A peptidic compound according to claim 1 having a length of up to 30 amino acid residues.

4. A peptidic compound according to claim 1 which has a linear or cyclic form.

5. A multimeric compound comprising a plurality of peptidic compounds as defined in claim 1.

6. The multimeric compound of claim 5 which is multimerized on a matrix, particularly selected from poly (N-alkyl (meth)acrylamide), poly (N,N-dialkyl(meth)acrylamide), polymelamine, dextrane, cyclodextrine, polyethyleneglycol and/or polyvinylpyrrolidone.

7. The multimeric compound of claim 5 which has a branched-structure.

8. The multimeric compound of claim 5, which is selected from:

(i) $R^1\text{—}(Y^1\text{—}R^1)_m\text{—}Y^1\text{—}(R^1)_{m'}$  (IIIa)

$R^1$ is a peptidic compound according to claim 1, $Y^1$ is a covalent bond or a bifunctional linker, and m is 0 or a positive whole number, and m' is 0 or 1, (ii) $[[(R^1)_{n1}Y^{1'}]_{n2}]Y^2$  (IIIb)

$R^1$ is a peptidic compound according to claim 1, $Y^{1'}$ is in each case independently a linker having a functionality of at least 3, and $Y^2$ is a linker having a functionality of at least 2, and $n_1$ and $n_2$ in each case independently are a whole number of at least 2, (iii) $\{[[(R^1)_{n1}Y^{1'}]_{n2}]Y^{2'}\}_{n3}Y^3$  (IIIc)

$R^1$ is a peptidic compound according to claim 1, $Y^{1'}$ and $Y^{2'}$ are in each case independent linkers having a functionality of at least 3, $Y^3$ is a linker having a functionality of at least 2 and $n_1$, $n_2$ and $n_3$ are in each case independently whole numbers of at least 2.

9. The multimeric compound of claim 8, wherein the multimeric compound (IIIb) comprises 4 peptidic units and has the structure

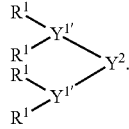

10. The multimeric compound of claim 9, wherein the multimeric compound (IIIb) has the structure $[[(R^1)_2Lys_2]_2]$-Lys-β-Ala.

11. The multimeric compound of claim 8, wherein $R^1$ is a compound selected from:

(ASLRVRIKKO)$_4$-Lys$_2$-Lys-β-Ala  (IV) and (ASLRVRIKK)$_4$-Lys$_2$-Lys-β-Ala  (V).

12. The compound of claim 1 which comprises at least one modification, particularly selected from a lipid, amide, ester, acyl and/or alkyl moiety attached thereto.

13. The compound of claim 12, comprising at least one lipid moiety, which is at least one amino carboxylic acid comprising a linear or cyclic, saturated mono- or polyunsaturated hydrocarbon group having 3 to 25 C-atoms, and which is preferably attached to the N- and/or C-terminus of the compound.

14. The compound of claim 1 having antipathogenic, in particular anti-viral activity against DNA and/or RNA viruses, in particular against herpes simplex, cytomegalovirus, human papilloma virus and human immunodeficiency virus.

15. A composition comprising the compound of claim 1, in combination with pharmaceutically acceptable carriers, diluents and/or adjuvants suitable for the treatment of pathogenic infections.

16. The composition of claim 15, wherein said pharmaceutically acceptable carriers, diluents and/or adjuvants are suitable for the treatment of a vaginally, rectally, orally sexually transmitted infection selected from one or more of the group consisting of herpes simplex, cytomegalovirus, human papilloma virus, human immunodeficiency virus, *chlamydia trachomatis* and *Neisseria gonorrhoeae*.

17. A composition comprising at least one compound as defined in claim 1 together with pharmaceutically acceptable carriers, diluents and/or adjuvants.

18. The composition of claim 17, wherein said pharmaceutically acceptable carriers, diluents and/or adjuvants are suitable for use in humans.

19. The composition of claim 17, wherein said pharmaceutically acceptable carriers, diluents and/or adjuvants are suitable for use in animals.

20. The composition of claim 17 in form of a pharmaceutical dosage form, selected from solids, liquids or gels and combinations thereof.

21. The composition of claim 17, further comprising at least one additional antipathogenic, in particular antiviral or/and antibacterial agent.

22. The composition of claim 21, wherein the additional antiviral agent is a protease inhibitor, a polymerase inhibitor, an integrase inhibitor, an entry inhibitor, an assembly/secretion inhibitor, a translation inhibitor, an immunostimulant or any combination thereof.

23. The multimeric compound of claim 7 which has a dendrimer structure.

24. The composition according to claim 15 wherein said pharmaceutically acceptable carriers, diluents and/or adjuvants are suitable for the prevention; and treatment of viral or/and bacterial infections.

25. The compound of claim 13, wherein said at least one amino carboxylic acid comprising a linear or cyclic, saturated mono- or polyunsaturated hydrocarbon group having 3 to 25 C-atoms is selected from the group consisting of 5-amino valeric acid, 5-amino pentanoic acid, 8-amino octanoic acid and 2-amino decanoic acid.

26. A peptidic compound according to claim 3 having a length of up to 15 amino acid residues.

27. The multimeric compound of claim 8, wherein said bifunctional linker is selected from the group consisting of
a dialcohol, a dicarboxylic acid, a diamine, an amino acid, a hydroxy carboxylic acid, and a diisocyanate, m is 1, 2, 3, 4, 5 or 6, $Y^{1'}$ and $Y^{2'}$ are in each case a trifunctional amino acid selected from the group consisting of lysine, ornithine, 2,4-diaminobutyric acid, nor-lysine, aminoalanine, aspartic acid and glutamic acid, and $n_1$, $n_2$ and $n_3$ are in each case independently 2, 3 or 4.

28. The multimeric compound of claim 8, wherein said bifunctional linker is selected from the group consisting of
propylene glycol succinic acid, and ethylene diamine, and/or $n_1$, $n_2$ and $n_3$ are in each case independently 2.

29. The composition of claim 20, wherein said composition is in the form of an eyewash, mouthwash, ointment, aerosol or topical product.

\* \* \* \* \*